United States Patent
Crainiceanu et al.

(10) Patent No.: US 9,607,392 B2
(45) Date of Patent: Mar. 28, 2017

(54) SYSTEM AND METHOD OF AUTOMATICALLY DETECTING TISSUE ABNORMALITIES

(71) Applicants: The Johns Hopkins University, Baltimore, MD (US); The United States of America, as represented by the Secretary Department of Health and Human Services, Washington, DC (US)

(72) Inventors: Ciprian M. Crainiceanu, Baltimore, MD (US); Elizabeth M. Sweeney, Baltimore, MD (US); Russell T. Shinohara, Baltimore, MD (US); Arthur J. Goldsmith, Baltimore, MD (US); Daniel Reich, Washington, DC (US); Colin Shea, Great Falls, VA (US)

(73) Assignee: The Johns Hopkins University, Baltimore, MD (US)

( * ) Notice: Subject to any disclaimer, the term of this patent is extended or adjusted under 35 U.S.C. 154(b) by 99 days.

(21) Appl. No.: 14/362,354

(22) PCT Filed: Dec. 5, 2012

(86) PCT No.: PCT/US2012/067997
§ 371 (c)(1),
(2) Date: Jun. 2, 2014

(87) PCT Pub. No.: WO2013/086026
PCT Pub. Date: Jun. 13, 2013

(65) Prior Publication Data
US 2015/0302599 A1  Oct. 22, 2015

Related U.S. Application Data

(60) Provisional application No. 61/630,101, filed on Dec. 5, 2011.

(51) Int. Cl.
*G06K 9/00* (2006.01)
*G06T 7/00* (2017.01)
(Continued)

(52) U.S. Cl.
CPC ............ *G06T 7/0081* (2013.01); *A61B 5/055* (2013.01); *A61B 5/7264* (2013.01); *A61B 6/032* (2013.01);
(Continued)

(58) Field of Classification Search
CPC . G06T 2207/10084; G06T 2207/20081; G06T 2207/20224; G06T 2207/30016; G06T 2207/30096; G06T 7/0016; G06T 7/0034
See application file for complete search history.

(56) References Cited

U.S. PATENT DOCUMENTS

2006/0074290 A1* 4/2006 Chen .................... G06T 7/0022
600/407
2006/0110018 A1 5/2006 Chen et al.
(Continued)

FOREIGN PATENT DOCUMENTS

WO  WO-2010-079519 A1  7/2010
WO  WO-2011-137370 A2  11/2011

OTHER PUBLICATIONS

Sweeney, E. M., et al. "Automatic lesion incidence estimation and detection in multiple sclerosis using multisequence longitudinal MRI." American Journal of Neuroradiology 34.1 (2013): 68-73.*
(Continued)

*Primary Examiner* — Bhavesh Mehta
*Assistant Examiner* — Ian Lemieux
(74) *Attorney, Agent, or Firm* — Venable LLP; Henry J. Daley

(57) ABSTRACT

A method of automatically detecting tissue abnormalities in images of a region of interest of a subject includes obtaining
(Continued)

first image data for the region of interest of the subject, normalizing the first image data based on statistical parameters derived from at least a portion of the first image data to provide first normalized image data, obtaining second image data for the region of interest of the subject, normalizing the second image data based on statistical parameters derived from at least a portion of the second image data to provide second normalized image data, processing the first and second normalized image data to provide resultant image data, and generating a probability map for the region of interest based on the resultant image data and a predefined statistical model. The probability map indicates the probability of at least a portion of an abnormality being present at locations within the region of interest.

27 Claims, 8 Drawing Sheets

(51) Int. Cl.
| | |
|---|---|
| A61B 5/055 | (2006.01) |
| A61B 5/00 | (2006.01) |
| A61B 6/03 | (2006.01) |
| A61B 8/00 | (2006.01) |
| G01R 33/48 | (2006.01) |
| G01R 33/50 | (2006.01) |
| G01T 1/16 | (2006.01) |
| G06F 19/00 | (2011.01) |
| G01R 33/56 | (2006.01) |

(52) U.S. Cl.
CPC .............. *A61B 6/037* (2013.01); *A61B 8/00* (2013.01); *G01R 33/4806* (2013.01); *G01R 33/50* (2013.01); *G01T 1/16* (2013.01); *G06F 19/345* (2013.01); *G06T 7/0012* (2013.01); *G06T 7/0016* (2013.01); *G06T 7/0034* (2013.01); *G06T 7/0087* (2013.01); *G01R 33/5602* (2013.01); *G01R 33/5608* (2013.01); *G06T 2207/10004* (2013.01); *G06T 2207/10081* (2013.01); *G06T 2207/10084* (2013.01); *G06T 2207/10088* (2013.01); *G06T 2207/10116* (2013.01); *G06T 2207/20081* (2013.01); *G06T 2207/20141* (2013.01); *G06T 2207/20224* (2013.01); *G06T 2207/30016* (2013.01); *G06T 2207/30096* (2013.01)

(56) References Cited

U.S. PATENT DOCUMENTS

| | | | | |
|---|---|---|---|---|
| 2008/0292164 | A1* | 11/2008 | Azar | .................... A61B 5/0091 382/131 |
| 2009/0279772 | A1* | 11/2009 | Sun | ...................... G06K 9/6298 382/141 |
| 2010/0016706 | A1 | 1/2010 | Wohlgemuth | |
| 2010/0128953 | A1* | 5/2010 | Ostrovsky-Berman | ................ G06T 7/0032 382/131 |
| 2010/0284595 | A1 | 11/2010 | Mori et al. | |
| 2010/0322488 | A1* | 12/2010 | Virtue | .................... A61B 5/055 382/128 |
| 2011/0013819 | A1* | 1/2011 | Raundahl | ............... G06K 9/527 382/132 |
| 2013/0243287 | A1* | 9/2013 | Thomson | .............. G06T 7/0081 382/128 |

OTHER PUBLICATIONS

Carass et al., (2007). A joint registration and segmentation approach to skull stripping. Biomedical Imaging: From Nano to Macro, 656-659.

Dodd et al., (2003). Partial AUC estimation and regression. Biometrics, 59(3), 614-23.

Duan et al., (2008). Segmentation of subtraction images for the measurement of lesion change in multiple sclerosis. AJNR. American journal of neuroradiology, 29(2), 340-6.

Filippi et al., (2011), M.A. MR imaging of multiple sclerosis. Radiology 259, 659-681.

Lucas et al., The Java Image Science Toolkit (JIST) for rapid prototyping and publishing of neuroimaging software (2010). Neuroinformatics 8, 5-17.

Moraal et al., (2009). Subtraction MR Images in a Multiple Sclerosis Multicenter Clinical Trial Setting. Radiology, 250(2), 506-514.

Moraal et al., (2010). Improved Detection of Active Multiple Sclerosis Lesions : 3D Subtraction Imaging. Radiology, 255(1), 155-163.

Polman et al., (2011). Diagnostic criteria for multiple sclerosis: 2010 revisions to the McDonald criteria. Annals of neurology, 69(2), 292-302.

Sahraian et al., (2007). MRI Atlas of MS Lesions. 1-178.

Shiee et al., (2010). A topology-preserving approach to the segmentation of brain images with multiple sclerosis lesions. NeuroImage, 49(2), 1524-35.

Shinohara et al., (2011). Population-wide principal component-based quantification of blood-brainbarrier dynamics in multiple sclerosis. NeuroImage, 57(4), 1430-46.

Simon et al., Standardized MR imaging protocol for multiple sclerosis: Consortium of MS Centers consensus guidelines (2006). AJNR Am J Neuroradiol 27, 455-461.

Tan et al., (2002). Original Communication Image registration and subtraction to detect active T 2 lesions in MS : an interobserver study. Annals of Neurology, 767-773.

International Search Report and Written Opinion of PCT/US2012/067997.

* cited by examiner

FIGS. 3A (top), 3B    FIGS. 3C (top), 3D

SYSTEM AND METHOD OF AUTOMATICALLY DETECTING TISSUE ABNORMALITIES

CROSS-REFERENCE OF RELATED APPLICATION

This is a national stage application under 35 U.S.C. §371 of PCT/US2012/067997 filed Dec. 5, 2012, the entire contents of which are incorporated herein by reference and this application claims priority to U.S. Provisional Application No. 61/630,101 filed Dec. 5, 2011, the entire content of which is hereby incorporated by reference.

This invention was made with Government support of Grant No. R01 N5060910-03/NINDS, awarded by the Department of Health and Human Services, The National Institutes of Health (NIH). The U.S. Government has certain rights in this invention.

BACKGROUND

1. Field of Invention

The field of the currently claimed embodiments of this invention relates to systems and methods for detection tissue abnormalities, and more particularly to systems and methods for detection tissue abnormalities from image data.

2. Discussion of Related Art

Multiple sclerosis (MS) is an inflammatory disease of the central nervous system, characterized by brain and spinal cord lesions. Although lesions in the gray matter of the brain are common, lesions are more readily recognized in the white matter (Sahraian et al., 2007). Magnetic resonance imaging (MRI) of the brain is used to detect lesions in MS and is essential in diagnosis and monitoring disease progression. In addition to documenting disease effects at one time, MRI can be used to assess longitudinal changes (Duan et al., 2008). MRI observation of lesion volume change resulting from the development of new lesions, enlarging lesions, and resolving lesions is an important marker of disease progression and response to therapy (Filippi et al., 2011). Lesion volume change is a common outcome in clinical trials and is computed by comparing radiologist manual segmentations of serial $T_2$-weighted MRI (Simon et al., 2006), which is time consuming and costly. Also, quantifying lesion change is challenging because such lesions represent only a small proportion of all lesions, typically on the order of 5-10% (Tan et al., 2002).

Images from consecutive studies can be registered, normalized and then subtracted to isolate areas of lesion change. In these subtraction images, radiologically stable disease related measurements are cancelled. Manually segmented two-dimensional $T_2$-weighted subtraction images identify a higher number of active lesions with greater inter- and intra-observer agreement (Tan et al., 2002) (Moraal et al., 2008) than comparing independently segmented serial images. However, these images are prone to artifacts from misregistration and partial volume effects (Duan et al., 2008). Subtraction images created from three-dimensional imaging acquisitions have better image quality and are less susceptible to registration errors. Subtraction images from various imaging modalities, such as three-dimensional double inversion-recovery, fluid-attenuated inversion recovery, $T_2$-weighted, and $T_1$-weighted volumes, have been shown to be less susceptible to the artifacts of two-dimensional subtraction images (Moraal et al., 2010). To our knowledge, no method for combining information from multiple modalities of MRI subtraction images has been developed.

Since subjects develop brain lesions over the natural course of multiple sclerosis, there is a need to identify, estimate the size of, and track, over the course of time, new lesions as they are being formed and remain in the brain. Currently, this is done manually by a trained neuroradiologist using slice-by-slice visual inspection. This process is very slow, can be prone to human error, and makes large observational studies of lesion development costly. Therefore, there remains a need for improved systems and methods for detection tissue abnormalities.

SUMMARY

A method of automatically detecting tissue abnormalities in images of a region of interest of a subject according to some embodiments of the current invention includes obtaining first image data for the region of interest of the subject, normalizing the first image data based on statistical parameters derived from at least a portion of the first image data to provide first normalized image data, obtaining second image data for the region of interest of the subject, normalizing the second image data based on statistical parameters derived from at least a portion of the second image data to provide second normalized image data, processing the first and second normalized image data to provide resultant image data, and generating a probability map for the region of interest based on the resultant image data and a predefined statistical model. The probability map indicates the probability of at least a portion of an abnormality being present at locations within the region of interest.

A computer-readable medium according to some embodiments of the current invention includes machine-executable code for automatically detecting tissue abnormalities in images of a region of interest of a subject. The machine-executable code, when executed by a computer, causes the computer to obtain first image data for the region of interest of the subject, normalize the first image data based on statistical parameters derived from at least a portion of the first image data to provide first normalized image data, obtain second image data for the region of interest of the subject, normalize the second image data based on statistical parameters derived from at least a portion of the second image data to provide second normalized image data, process the first and second normalized image data to provide resultant image data, and generate a probability map for the region of interest based on the resultant image data and a predefined statistical model. The probability map indicates the probability of at least a portion of an abnormality being present at locations within the region of interest.

A system for automatically detecting tissue abnormalities in images of a region of interest of a subject according to some embodiments of the current invention includes a signal processing unit configured to obtain first image data for the region of interest of the subject, normalize the first image data based on statistical parameters derived from at least a portion of the first image data to provide first normalized image data, obtain second image data for the region of interest of the subject, normalize the second image data based on statistical parameters derived from at least a portion of the second image data to provide second normalized image data, process the first and second normalized image data to provide resultant image data, and generate a probability map for the region of interest based on the resultant image data and a predefined statistical model. The probability map indicates the probability of at least a portion of an abnormality being present at locations within the region of interest.

BRIEF DESCRIPTION OF THE DRAWINGS

Further objectives and advantages will become apparent from a consideration of the description, drawings, and examples.

DETAILED DESCRIPTION

Figure 1:
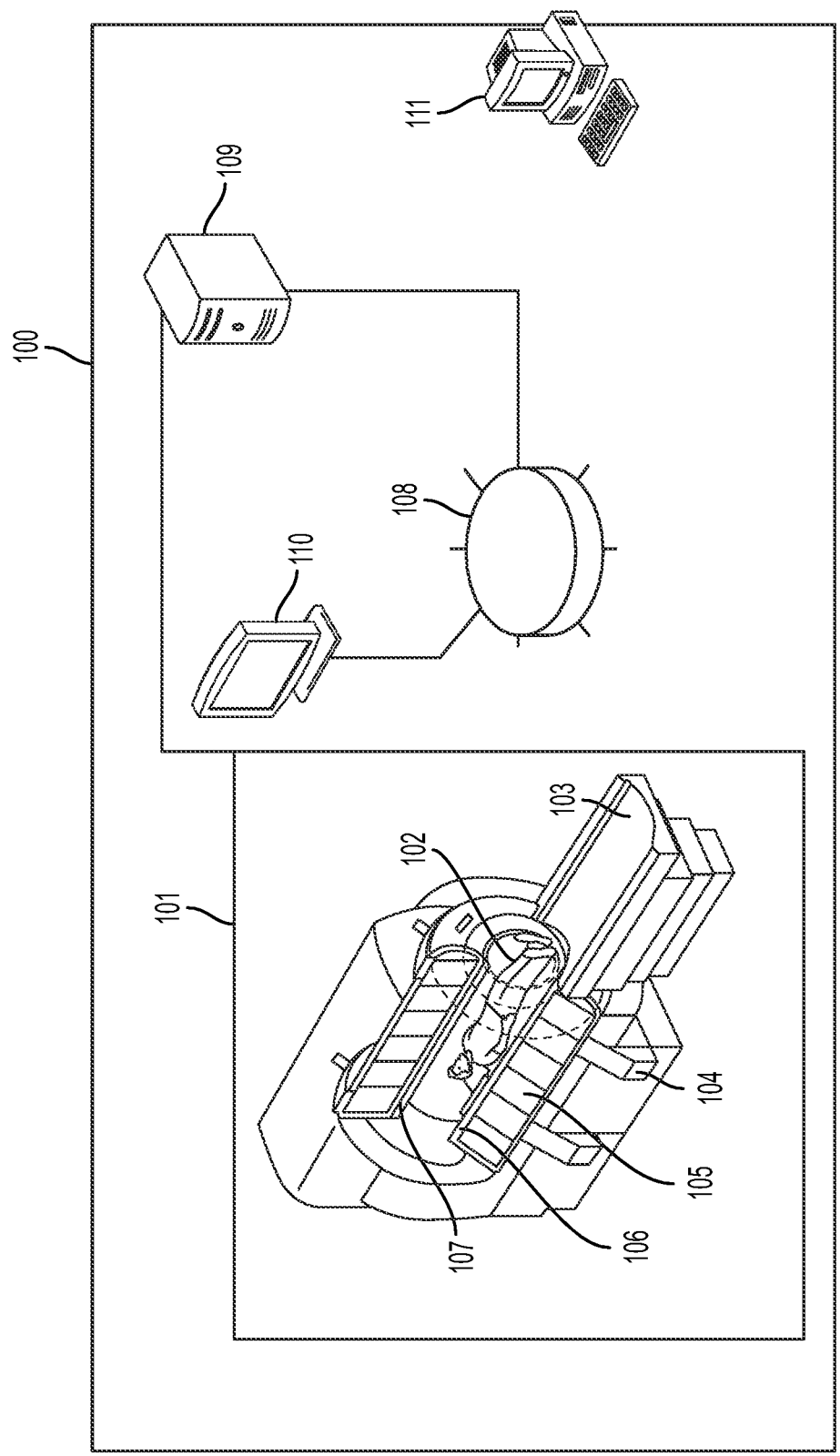
FIG. 1 is a schematic illustration of a system for automatically detecting tissue abnormalities in images of a region of interest of a subject according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Systems and methods according to some embodiments of the current invention can provide an automatic solution by incorporating information from multiple imaging modalities, a difficult task even for trained radiologists.

Some embodiments of the current invention provide novel systems and methods for automatically detecting lesion incidence in longitudinal brain magnetic resonance imaging (MRI) studies (data collected at multiple visits) using one or more imaging modalities. According to an embodiment of the current invention, Subtraction Based Logistic Inference for Modeling and Estimation (SuBLIME) uses multi-modality MRIs obtained at two studies and produces a voxel-level probability map of the brain that quantifies the likelihood that each voxel is part of an incident or enlarging lesion between the two studies. A validated probability threshold is then used to provide a binary lesion incidence map at every brain voxel. SuBLIME is a general method of incorporating multiple modalities for lesion detection and can be used with one or multiple MRI modalities, for example. SuBLIME was applied on MRI studies with only $T_2$-weighted images, as well as studies with $T_2$-weighted, $T_1$-weighted, fluid attenuated inversion recovery (FLAIR) and proton density (PD) MRI modalities. Currently there is no automatic procedure for detecting lesion incidence.

SuBLIME is a statistical model with several novel components according to some embodiments of the current invention. First, the method selects voxels with a higher probability of lesion incidence and only models on these candidate voxels according to an embodiment of the current invention. Second, it uses longitudinal data from multiple imaging modalities and can be tailored to the number of modalities available. The general concepts of the current invention are not limited to the particular number or types of imaging modalities used. Third, the method uses a robust normalization procedure, which allows it to be employed in large population samples and on previously unobserved subjects. Fourth, the method is fit on a training data set and checked on a validation set. Fifth, once the algorithm is trained, the actual lesion detection is very fast. Sixth, the method is robust to different scanning parameters and can easily be adapted to different magnetic field intensities.

Methods according to some embodiments of the current invention can be extended to MRIs acquired at different magnetic field intensity as well as different imaging modalities. The methods of SuBLIME can be adapted to whole brain segmentation for cross-sectional (single-visit/single subject), longitudinal data (multiple visits/single subject), and population longitudinal data (multiple subjects/multiple visits) using multiple modalities and statistical prediction algorithms.

FIG. 1A is a schematic illustration of a magnetic resonance imaging (MRI) system 100 according to an embodiment of the current invention. Other embodiments of the current invention can include other types of imaging systems instead of, or in addition to, MRI systems.

The MRI system 100 includes a magnetic resonance scanner 101, capable of imaging a subject 102 under observation on scanner bed 103. Magnetic resonance scanner 101 is located on base 104 and has a main magnet 105, a gradient coil system 106, and a radio-frequency (RF) coil system 107. Main magnet 105 provides a substantially uniform main magnetic field $B_0$ for subject 102. Gradient system 106 provides a perturbation of the main magnetic field $B_0$ to encode spatial information of the constituent water molecules with a region of interest of subject 102 under observation. The spatial information can be a spatial distribution of magnetizations, for example. Radio-frequency (RF) coil system 107 transmits RF pulses into a region of interest of subject 102 under observation and receives magnetic resonance (MR) response signals from subject 102. The region of interest can be, but is not limited to, a brain, a heart, a lung, a liver, a kidney, or other organs of interest in the thoracic or abdominal cavities, muscle or other tissue.

RF coil system 107 comprises at least one radio frequency (RF) coil configured to irradiate a radio frequency (RF) pulse into a region of interest of the subject 108. The RF coil can be, for example, a surface coil, a neck coil, an extremity coil, a head coil, a body, a phased-array coil, etc. The RF coil can be embodied as a solenoid, a planar coil, a volume coil, a quadrature coil, or variations thereof. The RF coil can be for transmission only or for both transmission and reception. RF coil system 107 can further comprise a power amplifier to amplify the RF pulse being transmitted or the received magnetic resonance signals. The power amplifier can be programmed or configured to amplify at more than one level of amplification. RF coil system 107 can further comprise matching and/or tuning networks for impedance matching and/or frequency tuning purposes.

The MRI system 100 can further include a data storage unit 108 and a signal processing unit 109. Data storage unit 108 is in communication with signal processing unit 109 to store signals from the region of interest of subject 102 under observation. The subject may be, for example, a human, an animal, a phantom, a sample, or combinations thereof. The region of interest may be, for example, a brain, a heart, a muscle, a liver, a kidney, a knee, a neck, etc.

Data storage unit 108 can be, for example, a hard disk drive, a network area storage (NAS) device, a redundant array of independent disks (RAID), a flash drive, an optical disk, a magnetic tape, a magneto-optical disk, etc. However, the data storage unit 108 is not limited to these particular examples. It can include other existing or future developed data storage devices without departing from the scope of the current invention.

Signal processing unit 109 is in communication with magnetic resonance scanner 101 to receive magnetic resonance signals from the region of interest in response to the RF pulse. Signal processing unit 109 can be partially or totally incorporated within a structure housing magnetic resonance scanner 101. Signal processing unit 109 can be at least partially incorporated in a workstation that is structurally separate from and in communication with magnetic resonance scanner 101. A workstation can be a computer having at least one central processing unit (CPU) and one memory, for example, static random access memory (SRAM), dynamic random access memory (DRAM), erasable programmable random access memory (EPROM), non-volatile flash memory, etc.

Signal processing unit 109 can be configured to reconstruct a plurality of images of the region of interest of the subject 108 based on the received RF response signals. Signal processing unit 109 can be further configure to retrieve stored signals and process the signals according to embodiments of the current invention that will be described in more detail below.

Output from signal processing unit 109 can be rendered on a display device, such as, for example, viewing station 110 or a console station 111. Viewing station 110 or console station 111 may be, for example, a cathode ray tube (CRT) monitor, a liquid crystal display (LCD) monitor, a digital light projection (DLP) monitor, a plasma screen, an organic light emitting diode (OLED), etc. The processed results may be used for further analysis and diagnosis.

EXAMPLES

The following presents some examples according some embodiments of the current invention. The broad concepts of the current invention are not limitation to the particular examples, which facilitate an explanation of some concepts and applications of embodiments of the current invention.

An embodiment of the current invention is referred to as Subtraction-Based Logistic Inference for Modeling and Estimation (SuBLIME) herein. SuBLIME is a fully automated and computationally fast method for segmenting voxel-level lesion incidence. Using a logistic regression model with various modalities of MRI from consecutive studies, we estimate the probability of lesion incidence in each voxel. The model utilizes information from the fluid attenuated inversion recovery (FLAIR), proton density (PD), $T_2$-weighted, and $T_1$-weighted images and subtraction images from these modalities. Using multi-modality data allows SuBLIME to be robust to the artifacts that plague traditional subtraction images. To show how multi-modality images improve lesion detection, we compare the full SuBLIME model to a nested model fit with only the $T_2$-weighted subtraction image.

Materials and Methods

Study Population

A total of 110 MRI studies (11 studies from ten subjects) were analyzed. All participants gave written consent and were scanned as part of an Institutional Review Board-approved natural-history protocol. Demographic, diagnosis, and treatment information can be found in Table 1.

TABLE 1

| Subject ID | Subtype | Age | Sex | EDSS | Treatment |
| --- | --- | --- | --- | --- | --- |
| 1 | RRMS | 37 | Male | 1.5 | Yes |
| 2 | RRMS | 38 | Female | 2.0 | Yes |
| 3 | RRMS | 48 | Male | 3.0 | No |
| 4 | RRMS | 38 | Female | 1.5 | No |
| 5 | RRMS | 30 | Female | 1.0 | Yes |
| 6 | RRMS | 43 | Female | 1.5 | Yes |
| 7 | RRMS | 35 | Female | 1.5 | Yes |
| 8 | RRMS | 37 | Female | 1.0 | Yes |
| 9 | RRMS | 47 | Female | 3.0 | Yes |
| 10 | RRMS | 56 | Female | 1.0 | No |

Experimental Methods

As part of different comprehensive protocols, we acquired whole brain two-dimensional FLAIR, PD, $T_2$-weighted, and three-dimensional T$_1$-weighted volumes in a 1.5 tesla MRI scanner (Signa Excite HDxt, GE Healthcare, Waukeska, Wis.), using the body coil for transmission. For signal detection, we used a volume head coil for 107 of the studies and an 8-channel receive coil (Invivo Corp, Gainsville, Fla.) in the remaining three studies. The two-dimensional FLAIR, PD, and T$_2$-weighted volumes were acquired using spin-echo sequences and the three-dimensional T$_1$-weighted volume using a GR sequence. The PD and T$_2$-weighted volumes were acquired as short and long echoes from the same sequence. We used various scanning parameters for the different studies. The ranges for the flip angle (FA), repetition time (TR), echo time (TE), and inversion time (TI) can be found in Table 2.

TABLE 2

| | FA (degrees) | TR (ms) | TE (ms) | TI (ms) |
|---|---|---|---|---|
| FLAIR | (90, 90) | (10,000, 10,000) | (77.8, 159.5) | (2200, 2500) |
| T$_2$-weighted, PD | (90, 90) | (3400, 6500) | (11.8, 15.0) | — |
| T$_1$-weighted | (13, 20) | (7.68, 10.3) | (1.88, 4.05) | (450, 750)* |

*106 of the T$_1$-weighted scans did not have an inversion time.

Image Post Processing

For the initial image processing, we used Medical Image Processing Analysis and Visualization (MIPAV) (http://mipay.cit.nih.gov) and Java Image Science Toolkit (JIST) (Lucas et al., 2010). We interpolated all images for each subject to a voxel size of 1 mm$^3$ and rigidly aligned the mean T$_1$-weighted volume to the Montreal Neurological Institute standard space. Then we registered the longitudinal collection of the T$_1$-weighted, T$_2$-weighted, FLAIR and PD images for the subject to this average image. We removed extracerebral voxels using a skull-stripping procedure (Carass et al., 2007). We automatically segmented the entire brain and the normal appearing white matter (NAWM) using the T$_1$-weighted and FLAIR images (Shiee et al., 2010).

Gold Standard Measure

To fit the model and to measure performance, we required a set of data in which the outcome is assessed using a gold standard measure. For the gold standard measure, we used an experienced neuroradiologist's segmentation of lesion incidence from consecutive T$_2$-weighted and FLAIR images and the T$_2$-weighted subtraction image. For each study, we segmented 5 representative axial slices of the brain: slices 50 (through the inferior temporal lobes, pons, and cerebellum), 70 (including the midbrain and occipital lobes), 90 (through the internal capsules), 110 (through the centrum semiovale), and 130 (near the vertex). In total there were 500 segmented slices with 55 incident or enlarging lesions.

Normalization

We performed all statistical modeling in the R environment (version 2.12.0, R Foundation for Statistical Computing, Vienna, Austria). We used intensities from the FLAIR, PD, T$_2$-weighted, and T$_1$-weighted volumes to identify new and enlarging lesions. We denote the observed intensity of voxel v, for subject i, from MRI study conducted at time t$_j$ by:

$$M_i^O(v,t_j), M=\text{FLAIR}, PD, T2, T1$$

where M indicates the imaging modality.

Analyzing images across study visits requires that the images be normalized so that voxel intensities have common interpretations. The normalization must allow for comparison of studies within and between subjects. Our aim was to segment incident lesions, which occur predominantly in the white matter; therefore it was natural to express intensities from each study as a departure from the subject's NAWM in each imaging modality (Shinohara et al., 2011):

$$M_i^N(v,t_j)=\{M_i^O(v,t_j)-\mu_{i,M}^O(t_j)\}/\sigma_{i,M}^O(t_j)$$

where $\mu_{i,M}^O(t_j)$ and $\sigma_{i,M}^O(t_j)$ are the mean and standard deviation of the observed voxel intensities in the NAWM of subject i, from modality M, conducted at time t$_j$. These normalized values are deviation measures from the mean intensity of the NAWM for a particular subject, study, and imaging modality, expressed in standard deviation units of the NAWM. The NAWM segmentations were developed using the high-resolution T$_1$-weighted and FLAIR images (Shiee et al., 2010). SuBLIME can use any NAWM segmentation approach and is not sensitive to the choice of segmentation algorithm. It may also be possible to normalize using the mean and standard deviation across the entire brain.

Subtraction Images

We calculated subtraction images for each modality by differencing consecutive normalized images. We denote the subtraction image intensity at voxel v for study t$_j$ by:

$$\Delta M_i^N(v,t_j)=M_i^N(v,t_j)-M_i^N(v,t_{j-1})$$

where i is the subject and M is the imaging modality. Improper registration, partial volume effects, and low signal-to-noise ratios can cause artifacts and noise in subtraction images; thus, using population-level thresholds to isolate lesions will typically lead to serious sensitivity and specificity losses in realistic scenarios. In contrast, SuBLIME was inherently designed to be pre-processing and artifact-resistant by: 1) borrowing strength and boosting the signal across multiple modalities; 2) using both baseline and longitudinal information; and 3) smoothing voxel-level prediction probabilities after logistic regression.

Subtraction-Based Logistic Inference for Modeling and Estimation

Figure 2:
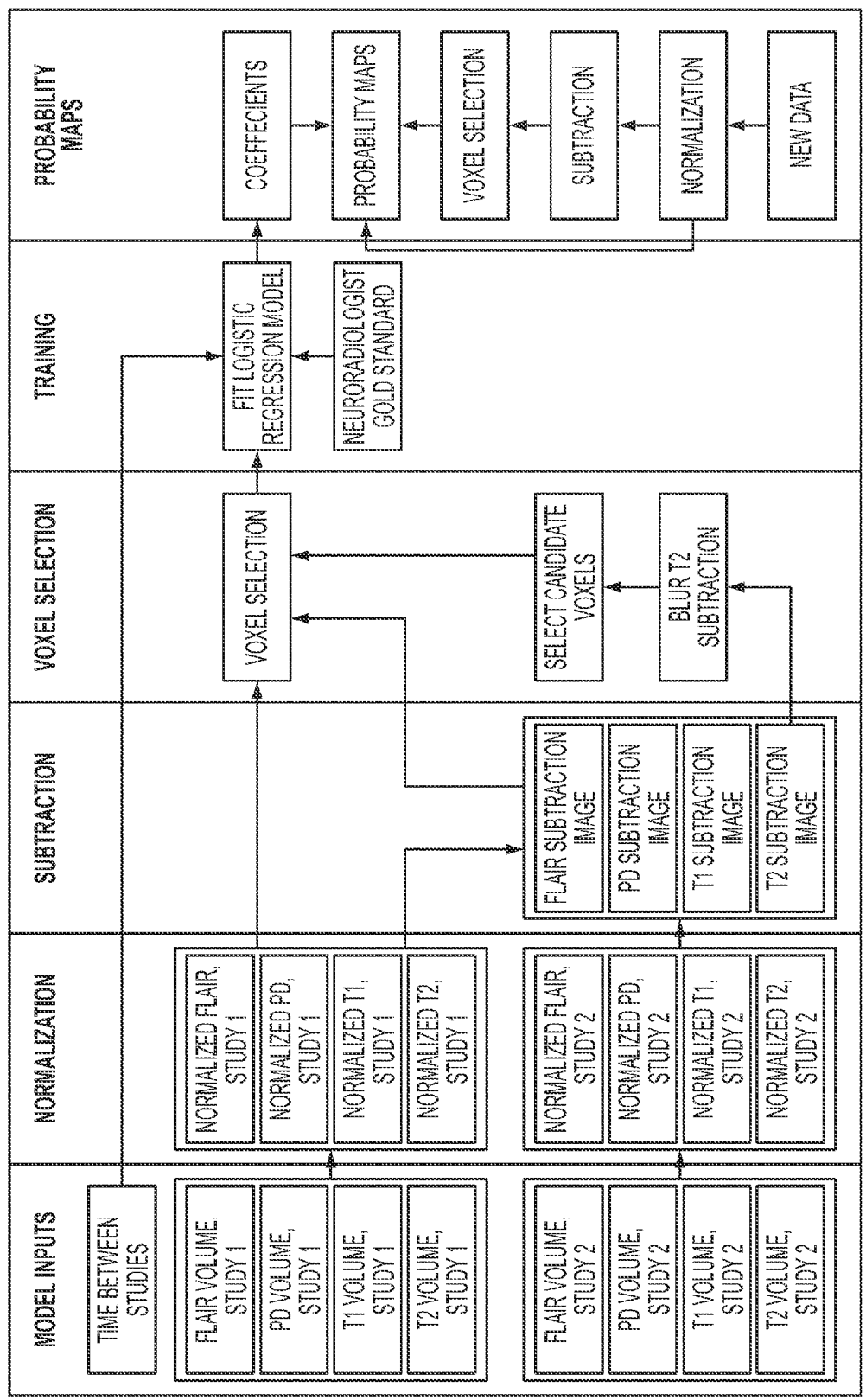
FIG. 2 is a flow chart describing a method of automatically detecting tissue abnormalities in images of a region of interest of a subject according to an embodiment of the current invention. This embodiment is referred to as SuBLIME. The chart is divided into six color-coded sections: model inputs, normalization, subtraction, voxel selection, training, and probability maps. The products of SuBLIME are probability maps of voxel level lesion incidence.

In this section, we introduce SuBLIME, which uses logistic regression to model the probability that a voxel is part of an incident or enlarging lesion. To limit false positive results, we exclude voxels with low T$_2$-weighted subtraction intensities. This includes much of the area of stable disease as well as areas of lesion repair that are characterized as hypointensities on the T$_2$-weighted subtraction image. We model lesion incidence at the voxel level using FLAIR, PD, T$_2$-weighted and T$_1$-weighted intensities from the later time point, the subtraction image intensities for each of these modalities, the time between the consecutive studies, and the interactions between the subtraction image intensities and the time between consecutive studies. The result of our model is a collection of coefficients that can be used to create three-dimensional maps of the probabilities of lesion incidence. FIG. 2 shows a flow chart describing SuBLIME. The chart is divided into six color-coded sections: model inputs, normalization, subtraction, voxel selection, training, and probability maps.

Figure 3:
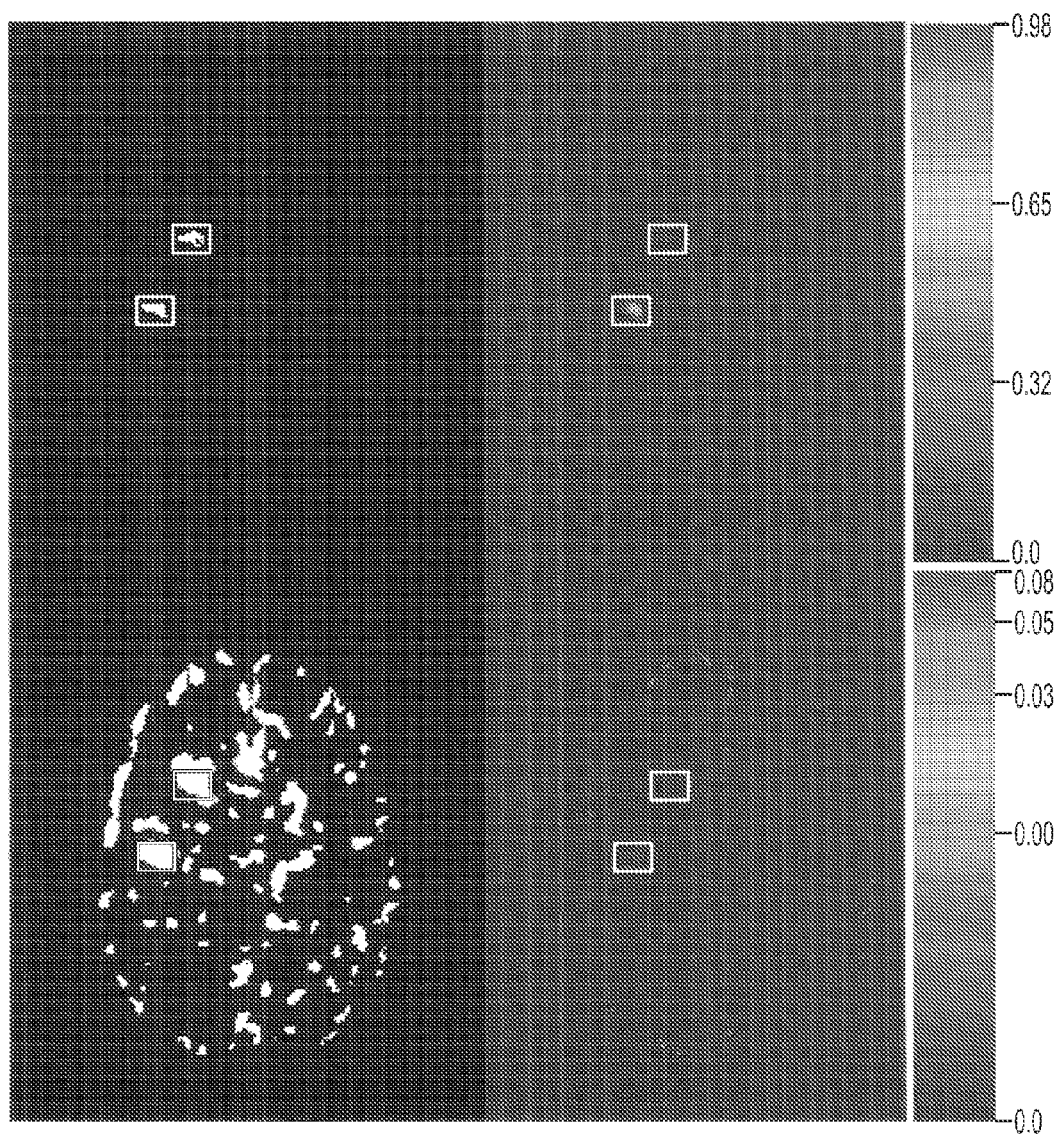
FIGS. 3A-3D show areas with lesion incidence are indicated with red boxes. A. Neuroradiologist's manual segmentation of an axial slice of the brain. B. Select voxels for SuBLIME modeling. C. Axial slice of the probability map from the full model. D. Axial slice of the probability map from the model fit with only the $T_2$-weighted subtraction image.

The first step of this procedure is to isolate candidate voxels that are likely to be part of incident lesions. As changes in lesion behavior are evident on T$_2$ subtraction images, we apply the logistic regression model only to voxels that are hyperintense on these images. To avoid isolated voxels that have high T$_2$ subtraction values as a result of noise, we smooth the subtraction image using a Gaussian kernel with window size of 5 mm. (We chose the kernel size empirically and found it to perform well.) Then, we include only voxels that have T$_2$ subtraction values larger than one standard deviation of the subtraction intensities calculated across the whole brain. (We chose the threshold of one standard deviation on the $T_2$ subtraction image empirically and found it to be liberal in capturing changes in lesions.) This is illustrated in FIGS. 3A-3D; FIG. 3A shows the radiologist segmentation of an axial slice of the brain, and FIG. 3B shows the candidate voxels for the same slice that will be used in the logistic modeling described below.

We then fit a voxel-level logistic regression model for lesion incidence over these candidate voxels, denoting the voxel-level lesion incidence by the random variable W:

$$W_i(v, t_j) = \begin{cases} 1, & \text{if subject } i \text{ has lesion incidence in voxel } v \text{ at time } t_j \\ 0, & \text{otherwise} \end{cases}$$

We model the probability that a voxel is part of a lesion incidence using the logistic regression model:

$$\log \text{it}[P\{W_i(v,t_j)=1\}] = \beta_0 + \beta_1 \Delta t + \beta_2 \text{FLAIR}_i^N(v,t_j) + \beta_3 \Delta \text{FLAIR}_i^N(v,t_j) + \beta_4 \Delta \text{FLAIR}_i^N(v,t_j) \times \Delta t + \beta_5 PD_i^N(v,t_j) + \beta_6 \Delta PD_i^N(v,t_j) + \beta_7 \Delta PD_i^N(v,t_j) \times \Delta t + \beta_8 T2_i^N(v,t_j) + \beta_9 \Delta T2_i^N(v,t_j) + \beta_{10} \Delta T2_i^N(v,t_j) \times \Delta t + \beta_{11} T1_i^N(v,t_j) + \beta_{12} \Delta T1_i^N(v,t_j) + \beta_{13} \Delta T1_i^N(v,t_j) \times \Delta t \quad (1)$$

where $\Delta t$ is the time in days between consecutive studies. The model is organized as a matrix with five rows and three columns and contains a total of 13 predictors. The second through fifth rows contain the intensity information from the FLAIR, PD, $T_2$-weighted and $T_1$-weighted volumes, respectively. The predictors in the first column of the model are the normalized intensities of each modality at study $t_j$, the variables in the second column are the subtraction images, and the third column consists of the interactions between the subtraction image and the change in time. This organization is especially useful for researchers who would like to change the model to adapt it to other specific problems. Note, however, that SuBLIME is a general logistic procedure encompassing a large number of logistic regression models. Here we use the specific model (1) because it performs very well in our application.

After we fit the model, we use the estimated coefficients to create maps of the estimated probability of lesion incidence at each voxel. To incorporate spatial information of the neighboring voxels and reduce noise, we smoothed the estimated probabilities from the model using a Gaussian kernel with window size of 3 mm. This kernel size was empirically chosen and found to perform well. An example of such a map using the full model is shown in FIG. 3C. An example of such a map using the nested model with only $T_2$-weighted subtraction is shown in FIG. 3D and is much noisier.

To assess the performance of the model, we randomly assigned five subjects to the training set and used the remaining five subjects for validation. All 10 subjects had 11 longitudinal studies. In the training set there were 26 incident and enlarging lesions; in the validation set there were 29. We fit model (1) on the training set subjects and visits and used only data from the validation set to estimate the voxel-level receiver-operator characteristic (ROC) curve and area under the curve (AUC).

Results

Figure 4:
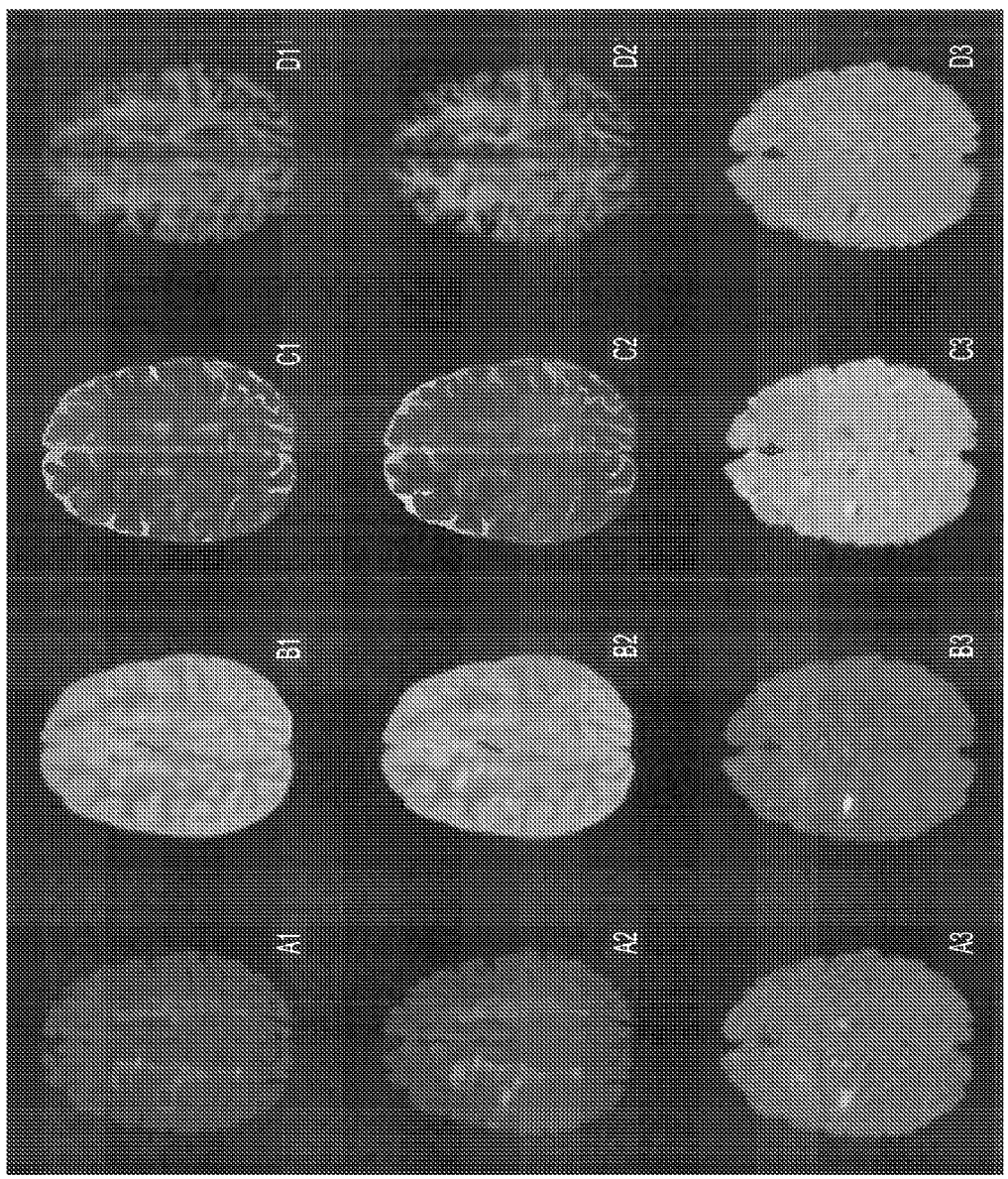
FIG. 4 shows axial slices from brain MRI of a single subject from two consecutive time points and the subtraction images created from these time points. Areas with lesion incidence between the two time points are indicated with red boxes. In the serial MRI images, lesions are characterized by hyperintensities in the FLAIR, PD, and $T_2$-weighted images and hypointensities in the $T_1$-weighted. In the subtraction images, lesion incidence and enlargement is characterized by hyperintensities in the FLAIR, PD, and $T_2$-weighted subtraction images and hypointensities in the $T_1$-weighted. A1. FLAIR at time one; A2. FLAIR at time two; A3. FLAIR subtraction image; B1. PD at time one; B2. PD at time two; B3. PD subtraction image; C1. $T_2$-weighted at time one; C2. $T_2$-weighted at time two; C3. $T_2$-weighted subtraction image; D1. $T_1$-weighted at time one; D2. $T_1$-weighted at time two; D3. $T_1$-weighted subtraction image.
Figure 5:
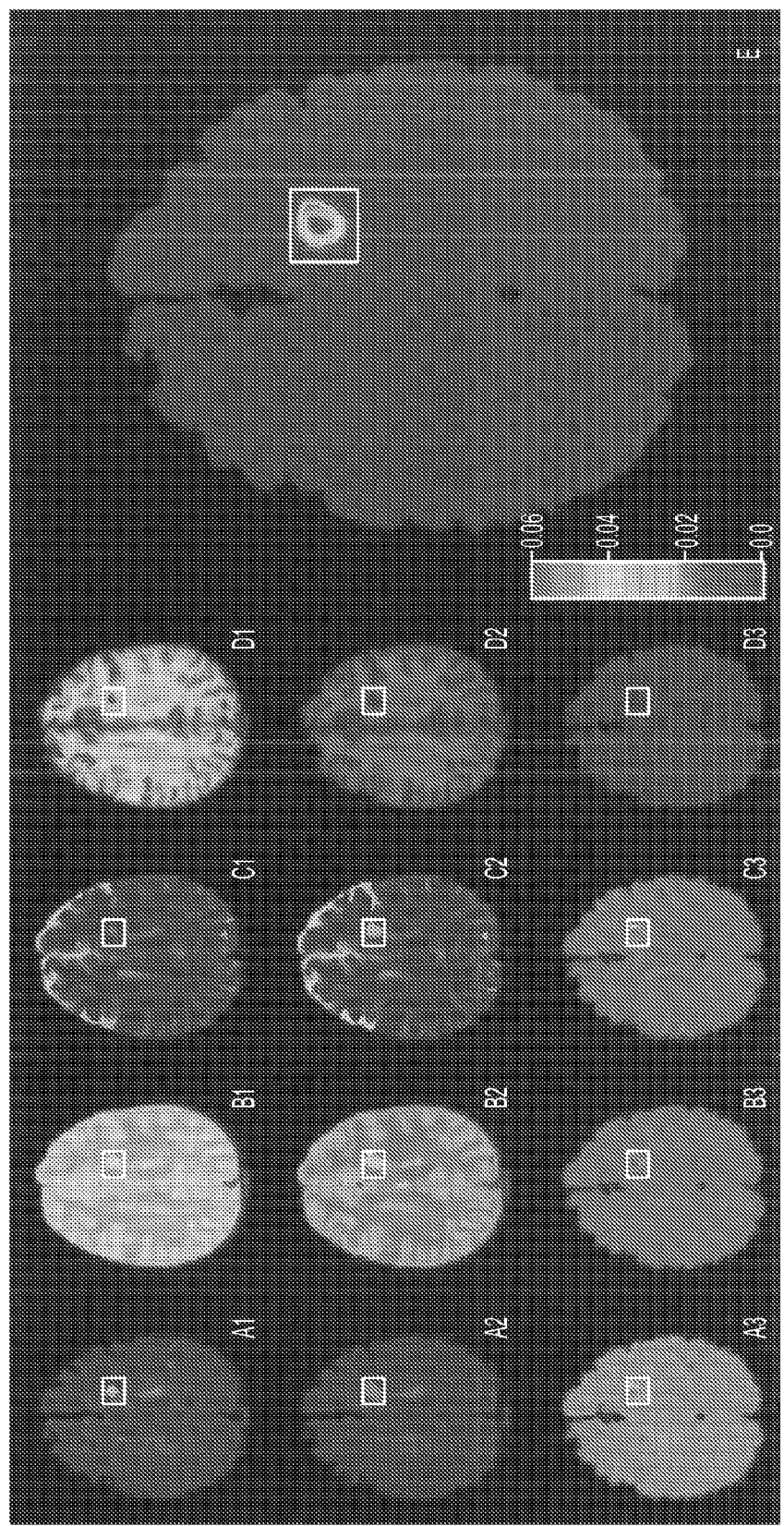
FIG. 5 shows axial slices from brain MRI of a single subject from two consecutive time points, the subtraction images created from these time points, and the probability map produced with the full model. An enlarging lesion is indicated in all images with a red box. A1. FLAIR at time one; A2. FLAIR at time two; A3. FLAIR subtraction image; B1. PD at time one; B2. PD at time two; B3. PD subtraction image; C1. $T_2$-weighted at time one; C2. $T_2$-weighted at time two; C3. $T_2$-weighted subtraction image; D1. $T_1$-weighted at time one; D2. $T_1$-weighted at time two; D3. $T_1$-weighted subtraction image; E. Probability map.

Axial slices from normalized FLAIR, PD, $T_2$-weighted, and $T_1$-weighted volumes from two consecutive studies performed on a single subject from the validation set are shown in FIG. 4. Lesions are characterized by hyperintensities in the FLAIR, PD, and $T_2$-weighted images and hypointensities in the $T_1$-weighted. One new and one expanding lesion are seen at the second study; these regions of interest (ROIs) are outlined. FIG. 4 also shows the subtraction images of the two studies for each modality. Lesion incidence is characterized by hyperintensities in the FLAIR, PD, and $T_2$-weighted subtraction images and by hypointensities in the $T_1$-weighted subtraction image. For the same subject and study, an axial slice of the smoothed probability map of lesion incidence from the full model is shown in FIG. 3C. FIG. 3D shows the same slice for a model fit with only the T2 subtraction image. Red indicates areas with the highest probability of lesion incidence and blue indicates areas with lower probabilities of lesion incidence. An axial slice of the probability map from the full model for another subject from the validation set is shown in FIG. 5E. The corresponding axial slice of the normalized FLAIR, PD, $T_2$-weighted, and $T_1$-weighted volumes from the two consecutive studies and the subtraction images are also shown in FIG. 5. The ROI indicates an enlarging lesion. This particular lesion is enlarging outward and is delineated as a ring on the probability map.

Figure 6:
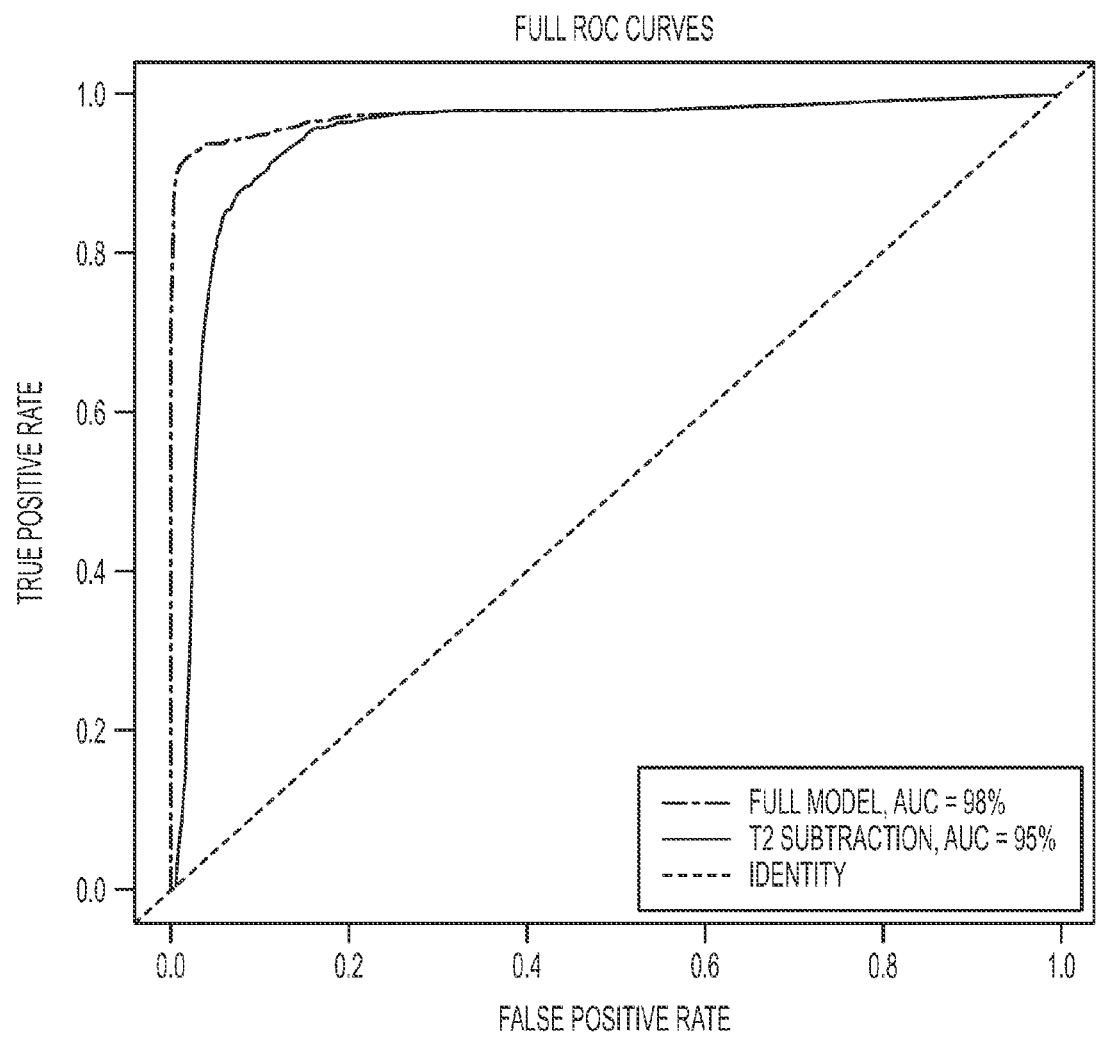
FIG. 6 shows ROC curves for the voxel-level detection of incident and enlarging lesions for different thresholds of the probability maps produced from SuBLIME. The lower ROC curve is for the full model and has an AUC of 98%. The upper ROC curve is for the model fit with only the $T_2$-weighted subtraction image and has an AUC of 92%.

The voxel-level ROC curve for the validation set is shown in FIG. 6. The vertical axis of the ROC curve shows the true positive rate for a given threshold on the probability map and the horizontal axis shows the false positive rate for this threshold. The upper curve is the ROC curve for the full model with an estimated AUC of 98%. The lower curve is the ROC curve for the model fit with only the $T_2$-weighted subtraction image with an estimated AUC of 95%.

The AUC calculated over the entire ROC space shown in FIG. 6 is not optimal for the evaluation of the performance of an algorithm designed to detect lesion incidence. This full AUC summarizes test performance over regions of the ROC space that are not clinically relevant. The subset of lesions showing change usually consists of a small fraction of all lesions in the brain, and an even smaller fraction of the entire brain. The average number of voxels in the brain among the training and validation set is 1,250,565. A false positive rate of 0.01 would correspond to a volume of 12,500 mm³ of healthy brain being falsely identified as lesion, making the resulting prediction maps difficult to interpret. Therefore, the performance of SuBLIME should only be evaluated for very small false positive rates; large false positive rates are not clinically relevant.

Let the partial AUC up to a given false positive rate fpr be defined as AUC(fpr). Dodd et al. (2003) noted that the partial AUC is difficult to interpret directly, and instead suggests the comparison of partial AUC odds:

$$\text{AUC}(fpr)/\{fpr - \text{AUC}(fpr)\}$$

Figure 7:
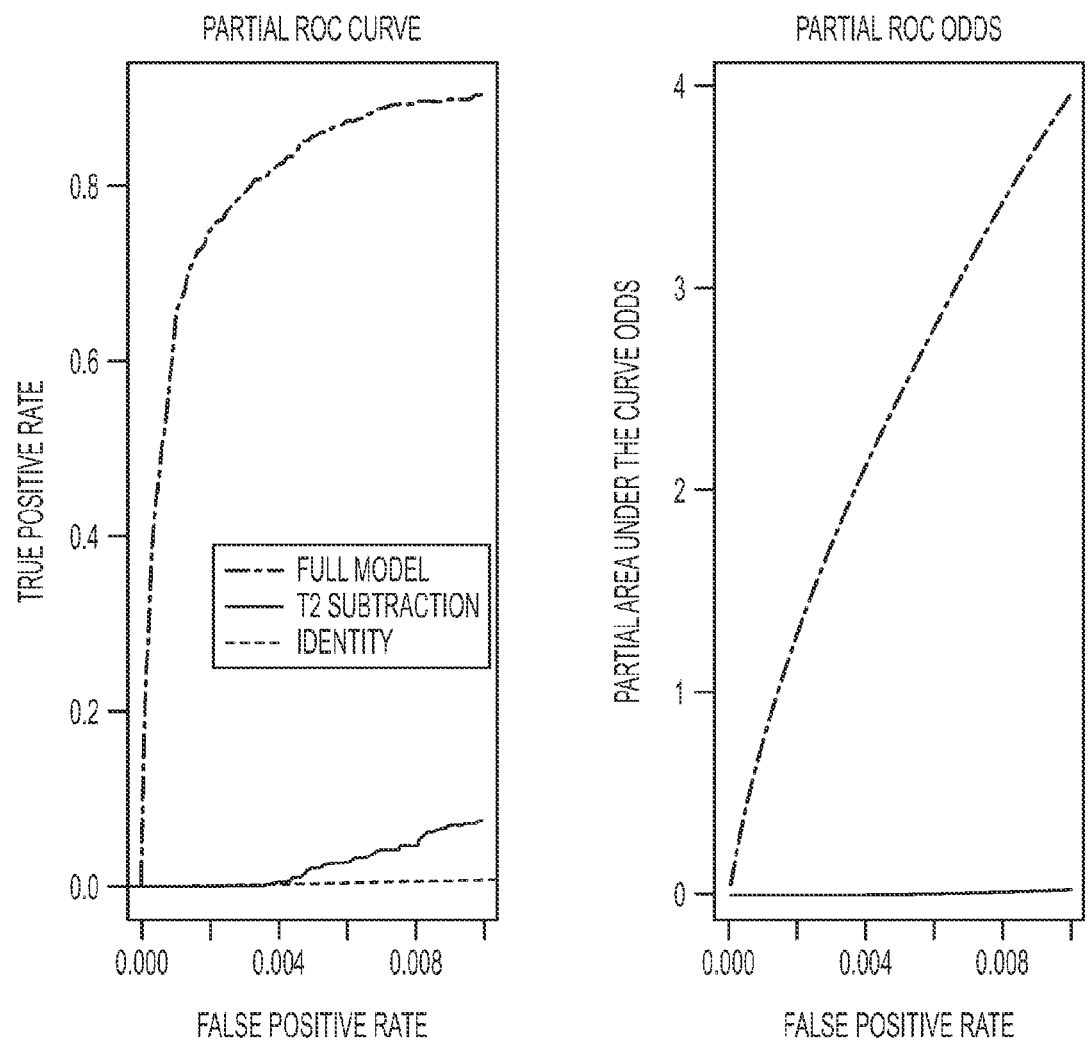
FIG. 7 shows plots of the partial ROC curve and partial AUC odds for false positive rates up to 0.01. The lower curve is for the full model and the upper curve is for the model fit with only the $T_2$-weighted subtraction image.

The partial AUC odds is the ratio of the probability of a correct ordering of a randomly selected lesion incident and non-lesion incident voxels to the probability of an incorrect ordering, with both probabilities conditional on the voxels of non-lesion incidence arising from the region with false positive rate less than or equal to fpr. A non-informative test will have a partial AUC odds of $(fpr)/\{2-(fpr)\}$ and a perfect test corresponds to an infinite value. FIG. 7 shows the partial ROC curve and the partial AUC odds for false positive rates up to 0.01. The upper curve corresponds to the full model (1) and the lower curve corresponds to the model fit with only the $T_2$ subtraction image. The full model has a much higher true positive rate and partial AUC odds for these relevant small false positive rates, which further emphasizes the importance of using the various modalities in addition to the $T_2$ weighted subtraction images.

Discussion

SuBLIME is an automated method that utilizes information from various imaging modalities to provide sensitive and specific segmentation of new and enlarging lesions. Lesion volume change is often an outcome in clinical trials for patients with MS and is traditionally assessed by manually segmenting consecutive MRIs. While the use of subtraction images in clinical trials has been discussed in the literature, these images are not routinely used in practice. In a clinical trial setting, our method may be used to replace manual segmentation of incident and enlarging lesions to reduce costs. After training, our fully automatic method does not require human input and thus avoids the variability introduced by manual segmentation. Training is necessary for each new dataset, but can be fairly limited as in the example from this paper.

The estimated coefficients from the full model based on all of the 10 subjects are given in Table 3. The coefficients for each modality are the log odds ratios of lesion incidence for voxels corresponding to an increased intensity of one normalized unit, fixing all other predictors. Lesions are characterized by hyperintensities in the FLAIR, PD, and $T_2$-weighted images and hypointensities in the $T_1$-weighted. As expected, the signs of coefficients for the FLAIR and PD intensities are positive. The coefficient of negative sign for the $T_2$-weighted and positive sign for the $T_1$-weighted are interpreted in the context where all other predictors are fixed. Due to the strong correlation among the imaging modalities, it is difficult to visualize the impact that a one standard deviation increase in the NAWM intensity in $T_2$-weighted or $T_1$-weighted images has on the log odds ratio when all other modalities are kept constant. The coefficients for the subtraction images have a similar interpretation. Lesion incidence is characterized by hyperintensities in FLAIR, PD, and $T_2$-weighted subtraction images and by hypointensities in $T_1$-weighted subtraction image. As expected, the signs of the coefficients for PD subtraction and $T_2$-weighted subtraction are positive, and $T_1$-weighted subtraction is negative. The sign for FLAIR subtraction is negative; this is again due to the correlation and must be interpreted while fixing all other predictors, including the $T_2$-weighted subtraction image. This may reflect the model's behavior in regions where registration is imperfect, especially near cerebrospinal fluid. The coefficients for the change in time and the interaction between the subtraction images and change in time were found to be small and in some cases not statistically significant. This can be attributed to the short time spans between scans; in studies with longer periods between study visits, changes in lesion load are more likely to occur and thus changes in the images may be more likely to indicate lesion incidence. The mean time between scans for the 110 MRI studies was 109 days and the median was 35 days. A histogram for the distribution for times between scans can be found in the FIG. 8. The coefficients of the nested model with only the $T_2$-weighted image can also be found in Table 3.

TABLE 3

The following is a summary of the full fitted model on a total of 1.3 million candidate voxels from 110 MRI studies of 10 subjects:

| | Coefficient | Standard Error | p value |
|---|---|---|---|
| Intercept | −9.1008 | 0.0706 | 0.000 |
| Δt | 0.0021 | 0.0001 | 0.0000 |
| FLAIR | 0.7388 | 0.0213 | 0.000 |
| ΔFLAIR | −0.0540 | 0.0278 | 0.0522 |
| ΔFLAIR × Δt | 0.0001 | 0.000 | 0.0078 |
| PD | 0.5606 | 0.0325 | 0.000 |
| ΔPD | 0.3959 | 0.0354 | 0.000 |
| ΔPD × Δt | −0.001 | 0.0001 | 0.1393 |
| T2 | −0.2531 | 0.0320 | 0.000 |
| ΔT2 | 0.6503 | 0.0381 | 0.000 |
| ΔT2 × Δt | −0.0003 | 0.000 | 0.0000 |
| T1 | 0.5098 | 0.0188 | 0.000 |
| ΔT1 | −0.8282 | 0.0258 | 0.000 |
| ΔT1 × Δt | 0.002 | 0.000 | 0.000 |

Figure 8:
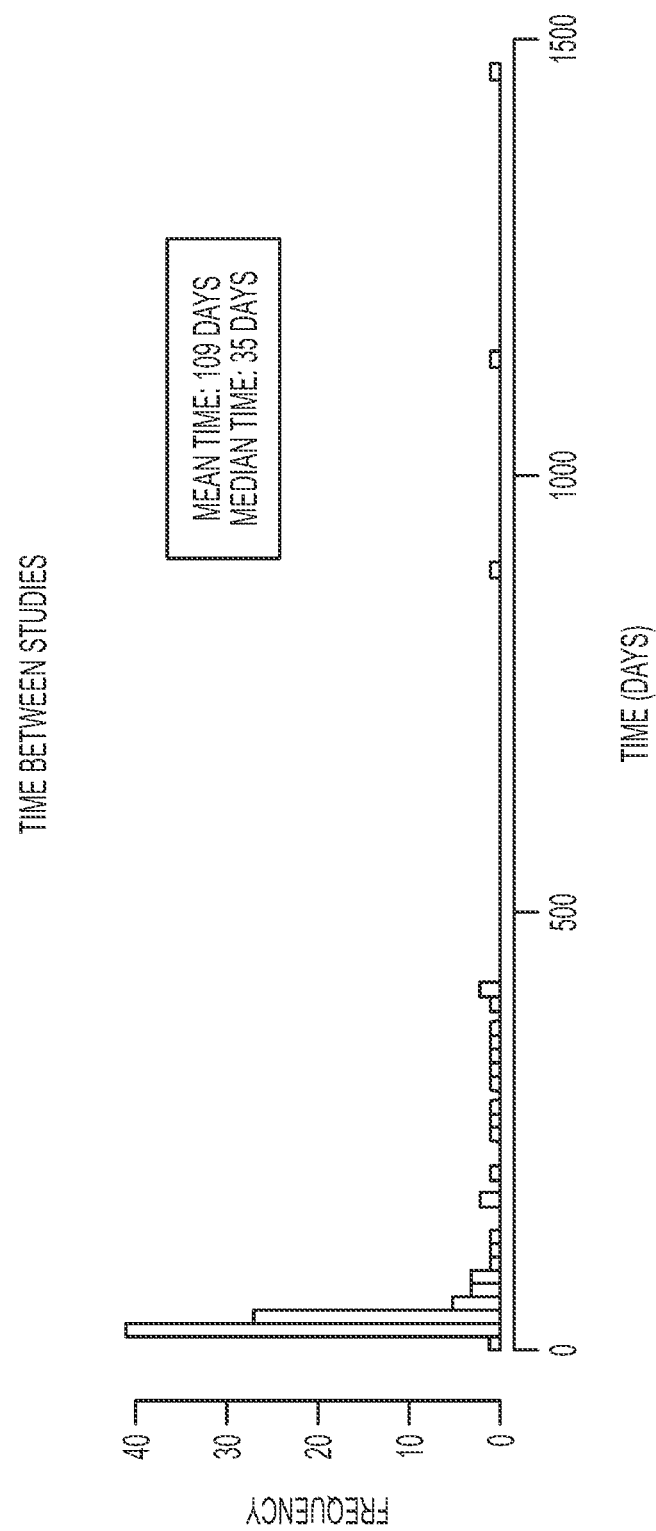
FIG. 8 provides a histogram for the distribution for times between scans for an example according to an embodiment of the current invention.

The histogram for time between studies for the 110 MRI studies is provided in FIG. 8.

We expect SuBLIME will be equally successful in segmenting lesion repair and shrinkage. Utilizing the information from the various imaging modalities and the subtraction images, a logistic regression model can be trained in a similar manner to detect lesion repair. Lesion recovery, like incidence, is visible in subtraction images where radiologically stable disease measurements are canceled. Recovery is characterized by hypointensities in FLAIR, PD, and $T_2$-weighted subtraction images and by hyperintensities in $T_1$-weighted subtraction image. Using SuBLIME to create models for incidence and recovery will allow fully automated lesion tracking (and the associated volumetric studies) longitudinally. In large observational datasets, our method facilitates the longitudinal study of the MS disease course.

In contrast to many automatic segmentation techniques, SuBLIME is computationally fast. Training the model on 5 slices from 110 images takes less than an hour on a standard workstation. This process is only conducted once after collecting a dataset that combines images from multiple protocols, and the results may be summarized as the 14 coefficients in model (1). Using this fitted model to generate a probability map from a set of new images takes seconds; the standard Gaussian smoothing is the slowest step of the algorithm. Other, faster smoothing methods may work just as well and could further improve the speed of the algorithm.

Because SuBLIME is fit voxel-wise, it is sensitive to major misregistration within a study and between longitudinal studies for the same subject. Poor registrations of images taken within a study visit and motion artifacts on the images can make the voxels incomparable across the modalities. Subtraction images will have artifacts if the longitudinal studies for a subject are poorly registered. However, SuBLIME is robust to minor errors in registration. By simultaneously comparing data from multiple modalities, SuBLIME distinguishes between artifacts and lesion incidence. As a result, it performs significantly better than simple thresholding of the subtraction images.

All of the studies used in this paper were acquired using 1.5 tesla MR scanners under different protocols. The analysis of MRIs acquired at higher field strengths or between different field strengths will likely yield different coefficients. We found SuBLIME to perform well on studies with different scanning parameters.

SuBLIME uses a voxel-level model for assessing the outcome. The assumption of independence between voxels is imperfect, as lesions consist of clusters of voxels. In this example, we use smoothing of the $T_2$-weighted subtraction image in candidate voxel selection, followed by a second smoothing of the predicted probabilities of the model to incorporate the spatial nature of the data. Nevertheless, further incorporation of neighboring voxel information is warranted.

Although developed for the particular application of longitudinal lesion incidence segmentation in MS, SuBLIME can be applied more generally to coregistered serial images to detect other changes and pathologies. We expect that a version of SuBLIME can be adapted to monitor other pathologies assessed using MRI, such as volumetric changes in patients with vascular disease or tumors. Our techniques may also be useful for monitoring changes in other imaging outcomes, including studies that use combinations of imaging techniques such as positron emission tomography-computed tomography studies in oncology. Finally, it is likely that the methods can be applied to organs outside the brain, including, but not limited to lung, liver, and kidneys.

REFERENCES

Carass, A., Wheeler, M. B., Cuzzocreo, J., Bazin, P. L., Bassett, S. S., Prince, J. L. (2007). A joint registration and segmentation approach to skull stripping. Biomedical Imaging: From Nano to Macro, 656-659.

Dodd, L. E., & Pepe, M. S. (2003). Partial AUC estimation and regression. Biometrics, 59(3), 614-23.

Duan, Y., Hildenbrand, P. G., Sampat, M. P., Tate, D. F., Csapo, I., Moraal, B, Bakshi, R., et al. (2008). Segmentation of subtraction images for the measurement of lesion change in multiple sclerosis. AJNR. American journal of neuroradiology, 29(2), 340-6.

Filippi, M. & Rocca (2011), M. A. MR imaging of multiple sclerosis. Radiology 259, 659-681.

Lucas, B. C. et al. The Java Image Science Toolkit (JIST) for rapid prototyping and publishing of neuroimaging software (2010). Neuroinformatics 8, 5-17.

Moraal, B., Meier, Dominik S, Poppe, P. A., Geurts, J. J. G., Vrenken, H., Knol, D. L., Schijndel, R. A. V., et al. (2009). Subtraction MR Images in a Multiple Sclerosis Multicenter Clinical Trial Setting. Radiology, 250(2), 506-514.

Morall, B., Wattjes, M. P., Knol, D. L., Schijndel, R. A. V., Pouwels, P. J. W., & Vrenken, H. (2010). Improved Detection of Active Multiple Sclerosis Lesions: 3D Subtraction Imaging. Radiology, 255(1), 155-163.

Polman, C. H., Reingold, S. C., Banwell, B., Clanet, M., Cohen, J. a, Filippi, M., Fujihara, K., et al. (2011). Diagnostic criteria for multiple sclerosis: 2010 revisions to the McDonald criteria. Annals of neurology, 69(2), 292-302.

Sahraian, A. M., & Radue, E. W. (2007). MRI Atlas of MS Lesions. 178

Shiee, N., Bazin, P.-L., Ozturk, A., Reich, D. S., Calabresi, P. a, & Pham, D. L. (2010). A topology-preserving approach to the segmentation of brain images with multiple sclerosis lesions. NeuroImage, 49(2), 1524-35.

Shinohara, R. T., Crainiceanu, C. M., Caffo, B. S., Gaitán, M. I., & Reich, D. S. (2011). Population-wide principal component-based quantification of blood-brain-barrier dynamics in multiple sclerosis. NeuroImage, 57(4), 1430-46.

Simon, J. H. et al. Standardized MR imaging protocol for multiple sclerosis: Consortium of MS Centers consensus guidelines (2006). AJNR Am J Neuroradiol 27, 455-461.

Tan, I. L., Schijndel, R. A. V., Miller, D. H., Pouwels, P. J. W., & Adèr, H. J. (2002). ORIGINAL COMMUNICATION Image registration and subtraction to detect active T 2 lesions in MS: an interobserver study Annals of Neurology, 767-773.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of automatically detecting tissue abnormalities in images of a region of interest of a subject, comprising:
    obtaining first image data for said region of interest of said subject;
    segmenting said first image data into a plurality of sub-images corresponding to a plurality of anatomical structures, each sub-image comprising a plurality of image elements;
    normalizing each sub-image of said first image data based on statistical parameters derived from said plurality of image elements within each corresponding sub-image to provide first normalized image data;
    obtaining second image data for said region of interest of said subject;
    segmenting said second image data into a plurality of sub-images corresponding to a plurality of anatomical structures, each sub-image comprising a plurality of image elements;
    normalizing each sub-image of said second image data based on statistical parameters derived from said plurality of image elements within each corresponding sub-image to provide second normalized image data;
    processing said first and second normalized image data to provide resultant image data; and
    generating a probability map for said region of interest based on said resultant image data and a predefined statistical model,
    wherein said probability map indicates the probability of at least a portion of an abnormality being present at locations within said region of interest.

2. The method of claim 1, wherein said predefined statistical model is a logistic regression model.

3. The method of claim 1, wherein said first image data and said second image data correspond to images taken at different times.

4. The method of claim 1, wherein said first image data and said second image data are for a single type of imaging modality.

5. The method of claim 4, wherein said single type of imaging modality is one of an MRI, X-ray computed tomography, positron emission tomography, single-photon emission computed tomography, or ultrasound.

6. The method of claim 4, wherein said single type of imaging modality is one of a proton density, fluid-attenuated inversion recovery, $T_2$-weighted, or $T_1$-weighted MRI imaging modality.

7. The method of claim 1, further comprising:
    obtaining third image data for said region of interest of said subject;

normalizing said third image data based on statistical parameters derived from at least a portion of said third image data to provide third normalized image data;

obtaining fourth image data for said region of interest of said subject;

normalizing said fourth image data based on statistical parameters derived from at least a portion of said fourth image data to provide fourth normalized image data;

processing said third and fourth normalized image data to provide a second resultant image data, wherein said generating said probability map for said region of interest is further based on said second resultant image data.

8. The method of claim 7, wherein said third image data and said fourth image data are for a single type of imaging modality that is a different imaging modality than said single imaging modality of said first and second imaging data.

9. A non-transitory computer-readable medium comprising machine-executable code for automatically detecting tissue abnormalities in images of a region of interest of a subject, said machine-executable code, when executed by a computer, causes the computer to:

obtain first image data for said region of interest of said subject;

segment said first image data into a plurality of sub-images corresponding to a plurality of anatomical structures, each sub-image comprising a plurality of image elements;

normalize each sub-image of said first image data based on statistical parameters derived from said plurality of image elements within each corresponding sub-image to provide first normalized image data;

obtain second image data for said region of interest of said subject;

segment said second image data into a plurality of sub-images corresponding to a plurality of anatomical structures, each sub-image comprising a plurality of image elements;

normalize each sub-image of said second image data based on statistical parameters derived from said plurality of image elements within each corresponding sub-image to provide second normalized image data;

process said first and second normalized image data to provide resultant image data; and generate a probability map for said region of interest based on said resultant image data and a predefined statistical model, wherein said probability map indicates the probability of at least a portion of an abnormality being present at locations within said region of interest.

10. The non-transitory computer-readable medium of claim 9, wherein said predefined statistical model is a logistic regression model.

11. The non-transitory computer-readable medium of claim 9, wherein said first image data and said second image data correspond to images taken at different times.

12. The non-transitory computer-readable medium of claim 9, wherein said first image data and said second image data are for a single type of imaging modality.

13. The non-transitory computer-readable medium of claim 12, wherein said single type of imaging modality is one of an MRI, X-ray computed tomography, positron emission tomography, single-photon emission computed tomography, or ultrasound.

14. The non-transitory computer-readable medium of claim 12, wherein said single type of imaging modality is one of a proton density, fluid-attenuated inversion recovery, $T_2$-weighted, or $T_1$-weighted MRI imaging modality.

15. The non-transitory computer-readable medium of claim 9, wherein said machine-executable code, when executed by said computer, further causes the computer to:

obtain third image data for said region of interest of said subject;

normalize said third image data based on statistical parameters derived from at least a portion of said third image data to provide third normalized image data;

obtain fourth image data for said region of interest of said subject;

normalize said fourth image data based on statistical parameters derived from at least a portion of said fourth image data to provide fourth normalized image data; and process said third and fourth normalized image data to provide a second resultant image data, wherein said generating said probability map for said region of interest is further based on said second resultant image data.

16. The non-transitory computer-readable medium of claim 15, wherein said third image data and said fourth image data are for a single type of imaging modality that is a different imaging modality than said single imaging modality of said first and second imaging data.

17. A system for automatically detecting tissue abnormalities in images of a region of interest of a subject, comprising:

a signal processor configured to:

obtain first image data for said region of interest of said subject;

segment said first image data into a plurality of sub-images corresponding to a plurality of anatomical structures, each sub-image comprising a plurality of image elements;

normalize each sub-image of said first image data based on statistical parameters derived from said plurality of image elements within each corresponding sub-image to provide first normalized image data;

obtain second image data for said region of interest of said subject;

segment said second image data into a plurality of sub-images corresponding to a plurality of anatomical structures, each sub-image comprising a plurality of image elements;

normalize each sub-image of said second image data based on statistical parameters derived from said plurality of image elements within each corresponding sub-image to provide second normalized image data;

process said first and second normalized image data to provide resultant image data; and generate a probability map for said region of interest based on said resultant image data and a predefined statistical model, wherein said probability map indicates the probability of at least a portion of an abnormality being present at locations within said region of interest.

18. The system of claim 17, further comprising a data storage device in communication with said signal processor.

19. The system of claim 18, further comprising an image acquisition system in communication with said signal processor and said data storage device.

20. The system of claim 19, wherein said image acquisition system is at least one of an MRI, X-ray computed tomography, positron emission tomography, single-photon emission computed tomography, or ultrasound imaging system.

21. The system of claim 17, wherein said predefined statistical model is a logistic regression model.

22. The system of claim 17, wherein said first image data and said second image data correspond to images taken at different times.

23. The system of claim 17, wherein said first image data and said second image data are for a single type of imaging modality.

24. The system of claim 23, wherein said single type of imaging modality is one of an MRI, X-ray computed tomography, positron emission tomography, single-photon emission computed tomography, or ultrasound.

25. The system of claim 23, wherein said single type of imaging modality is one of a proton density, fluid-attenuated inversion recovery, $T_2$-weighted, or $T_1$-weighted MRI imaging modality.

26. The system of claim 17, wherein said signal processor is further configured to:

obtain third image data for said region of interest of said subject;

normalize said third image data based on statistical parameters derived from at least a portion of said third image data to provide third normalized image data;

obtain fourth image data for said region of interest of said subject;

normalize said fourth image data based on statistical parameters derived from at least a portion of said fourth image data to provide fourth normalized image data; and process said third and fourth normalized image data to provide a second resultant image data, wherein said generating said probability map for said region of interest is further based on said second resultant image data.

27. The system of claim 26, wherein said third image data and said fourth image data are for a single type of imaging modality that is a different imaging modality than said single imaging modality of said first and second imaging data.

* * * * *

UNITED STATES PATENT AND TRADEMARK OFFICE
CERTIFICATE OF CORRECTION

PATENT NO. : 9,607,392 B2
APPLICATION NO. : 14/362354
DATED : March 28, 2017
INVENTOR(S) : Crainiceanu et al.

It is certified that error appears in the above-identified patent and that said Letters Patent is hereby corrected as shown below:

In the Specification

Column 1, Lines 14-18 replace with the following paragraph:
This invention was made with government support under NS060910 awarded by the National Institutes of Health. The government has certain rights in the invention.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*